(12) United States Patent
Brewer et al.

(10) Patent No.: US 6,225,635 B1
(45) Date of Patent: May 1, 2001

(54) SYSTEM AND METHOD FOR OPTICALLY LOCATING MICROCHANNEL POSITIONS

(75) Inventors: Laurence R. Brewer, Oakland; Joseph Kimbrough, Pleasanton; Joseph Balch; J. Courtney Davidson, both of Livermore, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/131,183

(22) Filed: Aug. 7, 1998

(51) Int. Cl.[7] ................................................. G01N 27/447
(52) U.S. Cl. ......................................... 250/458.1; 250/374
(58) Field of Search ................................. 250/458.1, 374

(56) References Cited

U.S. PATENT DOCUMENTS

| | | | |
|---|---|---|---|
| 4,707,235 | * 11/1987 | Englert et al. | 250/374 |
| 4,989,255 | * 1/1991 | Manns et al. | 382/8 |
| 5,293,365 | 3/1994 | Rokutan | 369/44.25 |
| 5,545,901 | 8/1996 | Pentoney, Jr. et al. | 250/458.1 |
| 5,608,211 | 3/1997 | Hirono et al. | 250/234 |
| 5,667,656 | * 9/1997 | Kambara | 250/458.1 |
| 5,675,155 | * 10/1997 | Pentoney, Jr. et al. | 250/458.1 |
| 5,784,152 | * 7/1998 | Heffelfinger et al. | 250/458.1 |
| 5,998,796 | * 12/1999 | Liu et al. | 250/458.1 |
| 6,039,925 | * 3/2000 | Nemoto | 250/458.1 |

FOREIGN PATENT DOCUMENTS

| | | |
|---|---|---|
| 93/17325 | 9/1993 | (WO) . |
| 96/29571 | 9/1996 | (WO) . |
| 98/10122 | 3/1998 | (WO) . |

* cited by examiner

Primary Examiner—Constantine Hannaher
Assistant Examiner—Otilia Gabor
(74) Attorney, Agent, or Firm—Lloyd E. Dakin, Jr.; Alan Thompson; Christopher J. Horgan

(57) ABSTRACT

A system and method is disclosed for optically locating a microchannel position. A laser source generates a primary laser beam which is directed at a microchannel plate. The microchannel plates include microchannels at various locations. A back-reflectance beam detector receives a back-reflected beam from the plate. The back-reflected beam is generated when the primary beam reflects off of the plate. A photodiode circuit generates a trigger signal when the back-reflected beam exceeds a predetermined threshold, indicating a presence of the microchannel. The method of the present invention includes the steps of generating a primary beam, directing the primary beam to a plate containing a microchannel, receiving from the plate a back-reflected beam generated in response to the primary beam, and generating a trigger signal when the back-reflected beam exceeds a predetermined threshold which corresponds to a presence of the microchannel.

30 Claims, 7 Drawing Sheets

SYSTEM AND METHOD FOR OPTICALLY LOCATING MICROCHANNEL POSITIONS

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates generally to systems and methods for locating microchannel positions, and more particularly for optically locating microchannel positions as part of a scanning DeoxyriboNucleic Acid (DNA) sequencer.

2. Discussion of Background Art

DNA sequencing is a technique used in conjunction with a national plan to decode the human genome in as little time as possible. The human genome is a very complex structure containing about three billion nucleic acid "base-pairs." Current DNA sequencing techniques involve placing DNA fragments onto a slab gel and separating the fragments so that base-pair information can be determined. Electrophoresis is a common technique used to separate the base-pair fragments from each other. The base-pairs can then be identified by various optical techniques that involve collecting a series of data points across the slab gel.

In efforts to speed up base-pair identification glass plates, having a set of microchannels, enable separation of several groups of DNA fragments in parallel. This technique requires collection of a very large number of optical measurement. Twelve-hundred to three-thousand data points may be taken during a single scan across such glass plates. A total amount of data taken for the entire glass plate may run in the one to eight gigabyte range.

Due to the large amount of data involved, modern DNA sequencers employ scanning devices and computers to collect the data. However, when the microchannel plates are not placed in their holders the same way each time, or plates with different microchannel formats are used, the computer controlled scanning devices will not work as intended. Furthermore, motors which drive the sequencer scanning devices often vary in speed and suffer from hysteresis, preventing accurate motor positioning during a scan. All of these effects hinder test result reproducibility, and limit efforts to reduce the amount of data collected.

In response to the concerns discussed above, what is needed is a system and method for optically locating a microchannel position that overcomes the problems of the prior art.

SUMMARY OF THE INVENTION

The present invention is a system and method for optically locating microchannel positions. Within the system of the present invention, a laser source generates a primary laser beam which is directed at a microchannel plate. The microchannel plates include microchannels at various locations. A back-reflectance beam detector receives a back-reflected beam from the plate. The back-reflected beam is generated when the primary beam reflects off of the plate. A photodiode circuit generates a trigger signal when the back-reflected beam exceeds a predetermined threshold, indicating a presence of a microchannel.

In another aspect of the invention, the photodiode circuit generates the trigger signal when the back-reflected beam exceeds a level corresponding to a gel-glass interface and falls below a level corresponding to an air-glass interface.

In another aspect of the invention, the photodiode circuit generates the trigger signal when the back-reflected beam exceeds a level corresponding to a glass-glass interface and falls below a level corresponding to a gel-glass interface.

And, in yet another aspect of the invention, the system collects and stores an entire set of back-reflectance beam data. A computer then analyzes the stored data to determine microchannel positions, using one or more of the techniques described above for generating trigger signals.

The method of the present invention includes the steps of generating a primary beam, directing the primary beam to a plate containing a microchannel, receiving from the plate a back-reflected beam generated in response to the primary beam, and generating a trigger signal when the back-reflected beam exceeds a predetermined threshold which corresponds to a presence of the microchannel.

In another aspect of the invention, the method further includes the steps of setting the predetermined threshold level below a back-reflected beam generated from an air-glass interface, and above a back-reflected beam generated from a gel-glass interface.

In another aspect of the invention, the method further includes the steps of setting the predetermined threshold level below a back-reflected beam generated from a gel-glass interface, and above a back-reflected beam generated from a glass-glass interface.

In another aspect of the invention, the method further includes the steps of receiving from the plate a fluorescence beam generated in response to the primary beam, and collecting a predetermined amount of fluorescence beam data in response to the trigger signal.

In a second embodiment of the invention, the method includes the steps of generating a primary beam, directing the primary beam to a plate containing a microchannel, receiving from the plate a back-reflected beam generated in response to the primary beam, collecting a predetermined amount of back-reflected beam data, and determining a position of the microchannel by analyzing the back-reflected beam data.

In the second embodiment of the invention, the method further includes the steps of receiving from the plate a fluorescence beam generated in response to the primary beam, collecting a predetermined amount of fluorescence beam data, and analyzing those fluorescence beam data points near the position of the microchannel.

The system and method of the present invention are particularly advantageous over the prior art because fluorescence data need only be taken when an optical detector of a DNA sequencer is positioned over the microchannels. This can reduce an amount of data that needs to be collected to perform DNA sequencing. Hysteresis and scanning velocity variation effects on data collection are also reduced. With the present invention, the position of the microchannels may be located even if the microchannel plate is not always placed in a same location.

These and other aspects of the invention will be recognized by those skilled in the art upon review of the detailed description, drawings, and claims set forth below.

DETAILED DESCRIPTION OF THE PREFERRED EMBODIMENT

Figure 1:
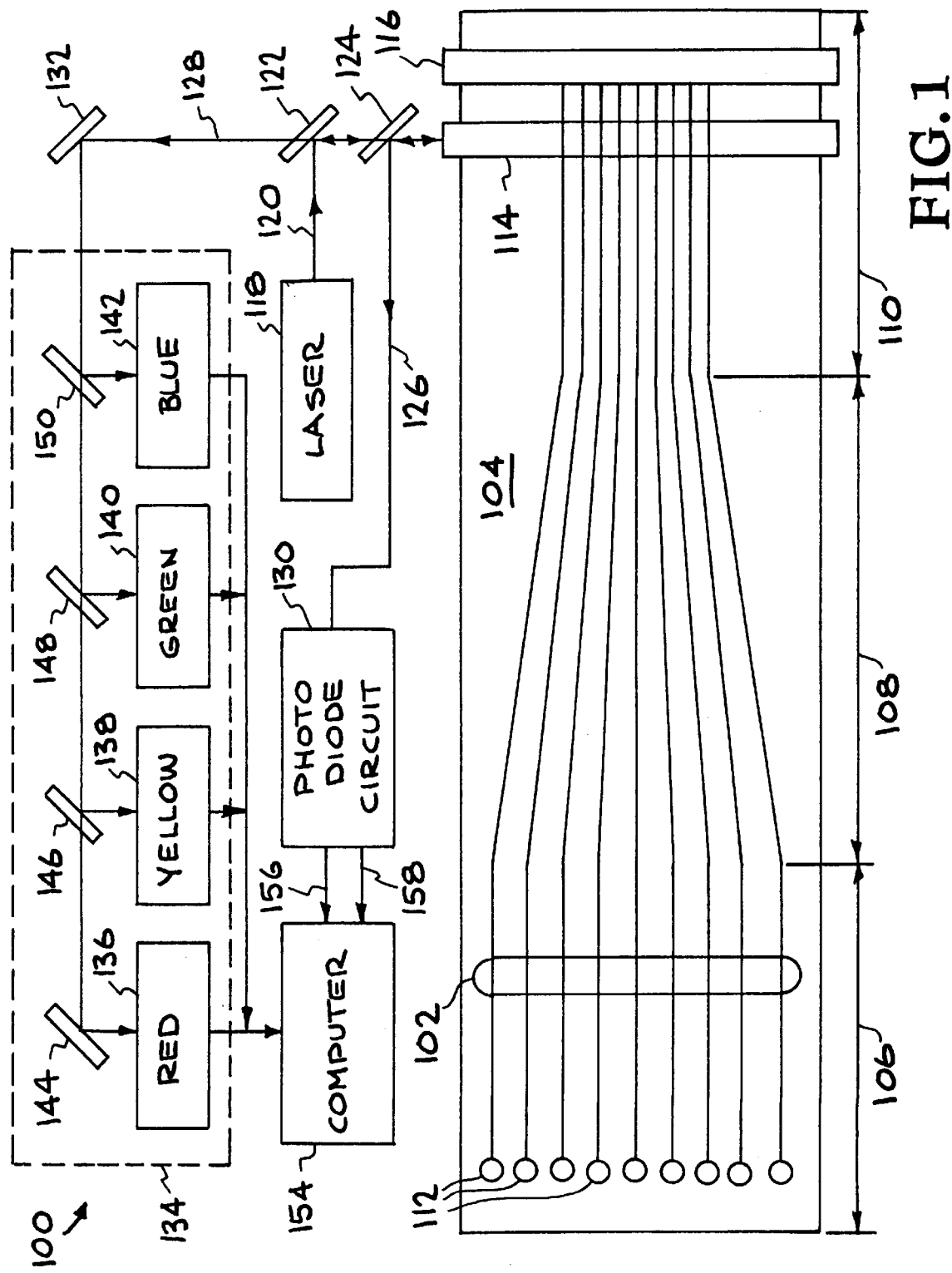
FIG. 1 is a block diagram of a system for optically locating microchannel positions according to the present invention.

FIG. 1 is a block diagram of a system 100 for optically locating microchannel 102 positions according to the present invention. The system 100 optically senses the position of the microchannel 102 on a microchannel plate 104 within a scanned, confocal, four-color, high-throughput DNA sequencer.

The microchannel plate 104 rests on a plate stand (not shown). The plate 104 can be divided into three different portions. In a first portion 106 of the plate 104, the microchannels 102 are separated by a first spacing. In a second portion 108, the microchannels 102 are tapering from the first spacing to a second spacing. And, in a third portion 110, the microchannels 102 are separated by the second spacing. Those skilled in the art will recognize that the plate 104 may differ in configuration from that described. For instance, the microchannel 102 spacing may be uniform throughout, or the plate 104 may be replaced by a capillary array.

In the first portion 106, receptacles 112 accept DNA fragments introduced from an outside source (not shown). Using electrophoresis techniques, an electric field, applied along a longitudinal axis of the plate 104, moves the DNA fragments through the microchannels 102 from the first portion 106 to the third portion 110. The microchannels 102 contain a sieving media to separate DNA fragments by length along the microchannels 102.

As the DNA fragments reach the third portion 110, a scanning assembly 114 collects data on the DNA fragments. The microchannels 102 are spaced more closely in the third portion 110 to minimize a distance over which the scanning assembly 114 must traverse to collect data on the fragments passing through the microchannels 102. By minimizing the distance, less time is required to scan the plate 104. After data collection is completed, a gel-pump 116, also in the third portion 110, forces clean sieving media and various other buffered solutions through the microchannels 102, to clean out the DNA fragments.

The scanning assembly 114 collects data by directing a primary laser beam 120, generated by a laser 118. The primary beam 120 is a collimated Argon-ion laser beam in the 488 nm range. Before reaching the scanning assembly 114, the primary beam 120 is optically directed through a shutter assembly (not shown), beam forming lenses (not shown), a dichroic mirror 122, and a microscope cover-slip 124. The scanning assembly 114 then directs the primary beam 120 onto the plate 104, illuminates the microchannels 102, and the DNA fragments within.

The scanning assembly consists of a scanning Laser Induced Fluorescence (LIF) detector, and a linear motor. The LIF detector includes a mirror which reflects the primary beam 120 through a high Numerical Aperture (NA=0.6) lens. The lens focuses the primary beam 120 down to a diffraction limited spot on the microchannel plate 104. As the linear motor moves the scanning assembly 114 perpendicular to a longitudinal axis of the plate 104, the diffraction limited spot of the primary beam 120 reflects from any glass—glass, air-glass, or gel-glass interface, generating a back-reflected beam 126. During scanning, the diffraction limited spot also excites dye-tags coupled to the DNA fragments. These dye-tags fluoresce when illuminated, generating a fluorescence beam 128.

The fluorescence beam 128 is optically directed back to a confocal fluorescence detector assembly 134 after passing through the microscope cover-slip 124, the dichroic mirror 122, and an additional mirror 132. The dichroic mirror 122 separates out the fluorescence beam 128 from the primary beam 120. The fluorescence detector assembly 134 routes the fluorescence beam 128 to a red 136, yellow 138, green 140, and blue 142 photomultiplier tube through a set of mirrors 144, 146, 148, 150. These tubes 136 through 142 amplify a particular wavelength of light and pass a corresponding light amplitude signal over a cable 152 to an analog to digital converter board in a computer 154 for processing.

The back-reflected beam 126 is optically directed back to a photodiode circuit 130 after passing through the microscope cover-slip 124. The microscope cover-slip 124 is inserted into the beams 120, 126 and 128 at a 45 degree angle. With an anti-reflective coating, and a wedged shaped cross-section (i.e. the cover-slip 124 surfaces are not parallel), the microscope cover-slip 124 separates out the back-reflected beam 126 from the combined beams 120, 126, and 128. The back-reflected beam 126 is then passed to the photodiode circuit through an adjustable iris (not shown). The photodiode circuit 130 transforms the back-reflected beam 126 into an electrical signal which is sent over line 156 to the computer 154. The photodiode circuit 130 also generates a trigger signal which is passed to the computer 154 over line 158. As will be further discussed infra., these two signals control how the computer 154 collects and processes data received from the confocal fluorescence detector assembly 134 over the cable 152.

The computer 154 is preferably of a type conventionally known in the art. The computer 154 includes an internal memory (not shown) for storing computer program instructions which control how a processing unit (not shown) within the computer accesses, transforms and outputs data. The internal memory includes both a volatile and a non-volatile portion. Those skilled in the art will recognize that the internal memory could be supplemented with other computer usable storage media, including a compact disk, a magnetic drive or a dynamic random access memory. The processing instructions contained within the computer 154 are further discussed with respect to FIGS. 6, 7, and 8. Each of the system 100 elements, except for the computer 154 are preferably enclosed within a light-tight enclosure (not shown).

Figure 2:
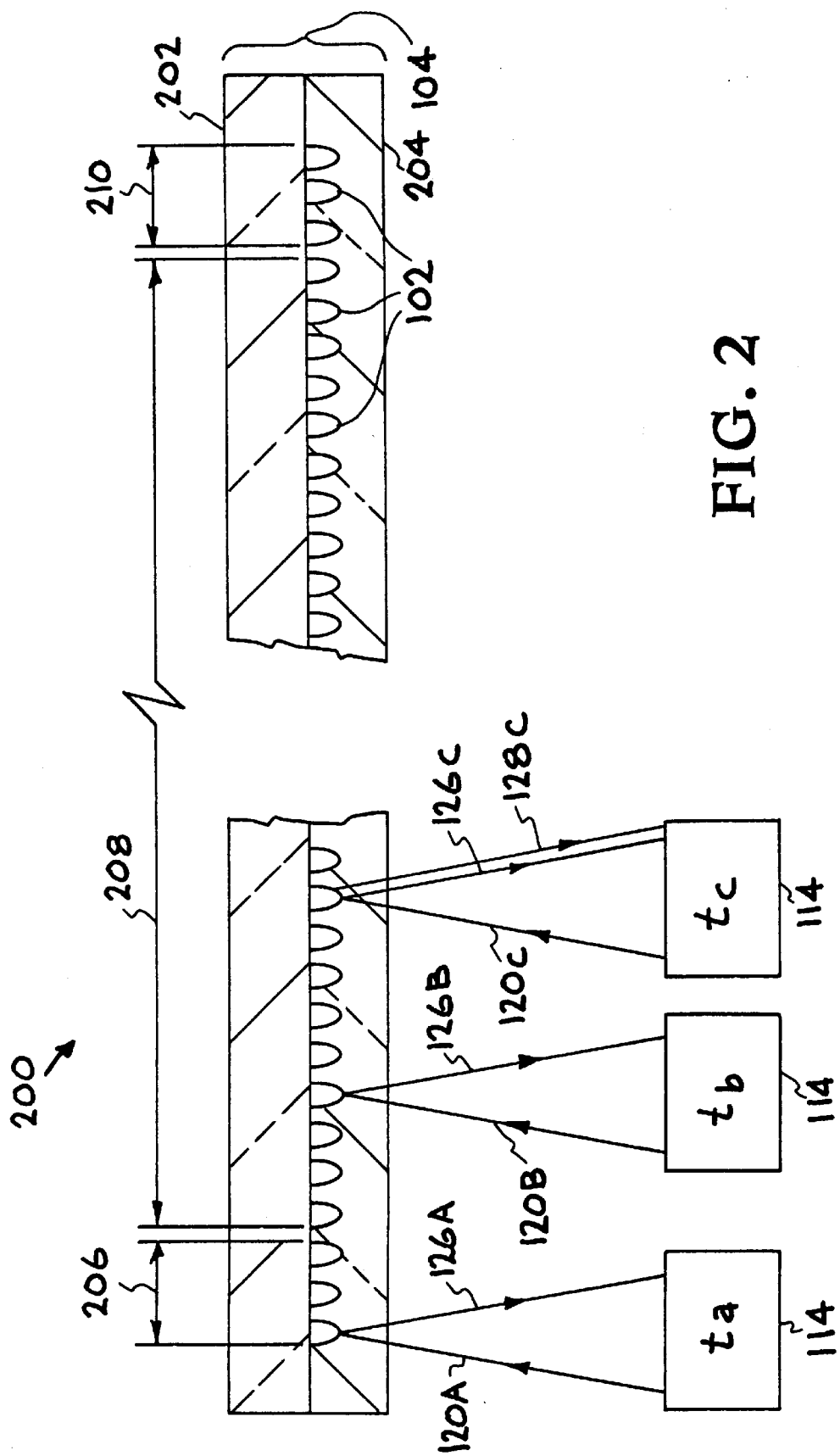
FIG. 2 is a pictorial diagram of a cross-section of a microchannel plate in the system of FIG. 1.

FIG. 2 is a pictorial diagram of a cross-section 200 of a microchannel plate 104 in the system of FIG. 1. The plate 104 consists of a top glass plate 202 and a bottom glass plate 204, each plate 202 and 204 is about 58 cm in length, 7.5 cm in width, and 9 mm in thickness. The plate 104 may have any number of microchannels 102, however, typically the plate 104 will have from 24 to 96 microchannels 102. The microchannels 102 are approximately tetrahedral in cross section, 200 μm across at the top, 100 μm at the bottom, and 50 μm deep. The microchannel spatial period is approximately 300 μm. Those skilled in the art will recognize that the plate 104 and the microchannels 102 may be of dimensions other than those describe here. The top and bottom plates 202 and 204 are flip-bonded together. Flip-bonding refers to a process where the top plate 202 rests on a surface within a kiln, but the bottom plate 204 remains in contact with only the gases in the kiln. Flip-bonding is preferred since the primary beam 120 preferably illuminates the bottom plate 204, and flip-bonding minimizes scattered light originating from an outer surface of the bottom plate.

In the cross-section 200, a first outer set 206, a middle set 208, and a second outer set 210 of microchannels 102 are shown. The first and second outer sets 206 and 210 are filled with air. The middle set 208 is filled with the gel sieving media. The scanning assembly 114 is shown as it scans the plate 104 at three different times $t_A$, $t_B$, and $t_C$. At time $t_A$, the scanning assembly 114 transmits primary beam 120A to one of the air-glass interfaces in the first set 206, resulting in a first back-reflectance beam 126A. At time $t_B$, the scanning assembly 114 transmits primary beam 120B to one of the glass-glass interfaces in the middle set 208, resulting in a second back-reflectance beam 126B. At time $t_C$, the scanning assembly 114 transmits primary beam 120C to one of the gel-glass interfaces in the middle set 206, resulting in a fluorescence beam 128C and third back-reflectance beam 126C. The fluorescence beam 128C come from the excited dye-tagged DNA fragments within the gel. It is by differences between the first, second, and third reflectance 126A, B, and C that the system 100 may identify where the microchannels 102 are located within the plate 104. This microchannel 102 detection schema is also operable if metalized stripes are formed between microchannels 102 within the plate 104 during the flip-bonding process.

Figure 3:
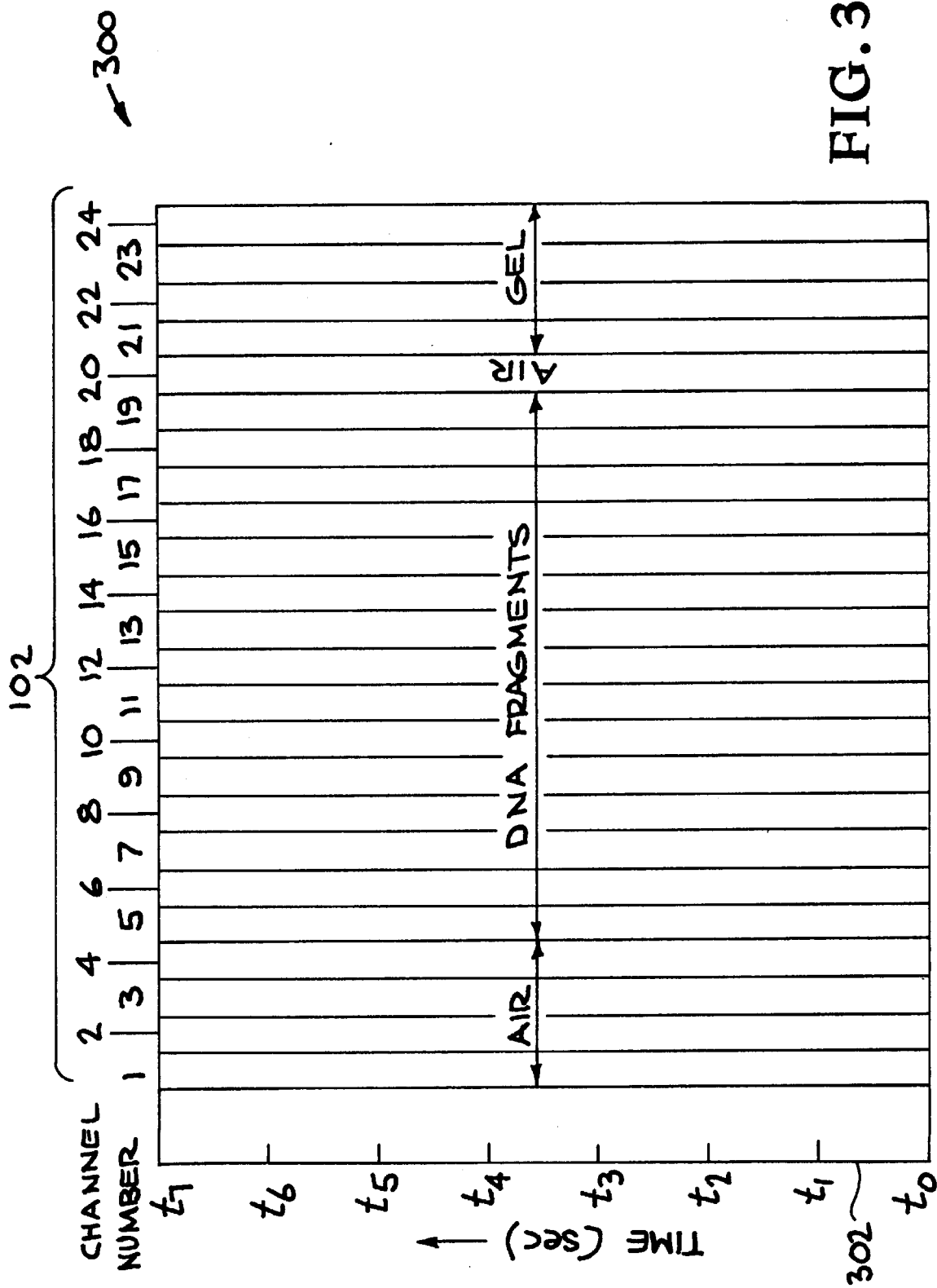
FIG. 3 is a computer generated graph of DNA fragments as they electrophorese through a plurality of microchannels within the microchannel plate.

FIG. 3 is a computer generated graph 300 of the DNA fragments as they over time 302 electrophorese through the plurality of microchannels 102 within the microchannel plate 104. In the graph 300 an exemplary set of twenty-four microchannels 102 are shown over a time period $t_0$ through $t_7$. Microchannels 1–4, and 20 are filled with air, microchannels 5–19 are filled with gel and DNA fragments, and microchannels 21–24 are filled only with gel. As the scanning assembly 114 moves perpendicular to the channels and the DNA fragments electrophorese past the scanning assembly 114 over time, the graph 300 shown is generated. Each of the microchannels 102 have a channel-width 304 and are separated by a channel spacing 306.

In the example shown, channels 1–4, and 20 are empty, channels 5–19 are filled with gel and DNA fragments, and channels 21–24 are filled with gel only. At time $t_0$ a primer in microchannels 5 through 19 moves past the scanning assembly 114 first. From times $t_1$ through $t_7$, the other DNA fragments move past the scanning assembly 114.

Figure 4:
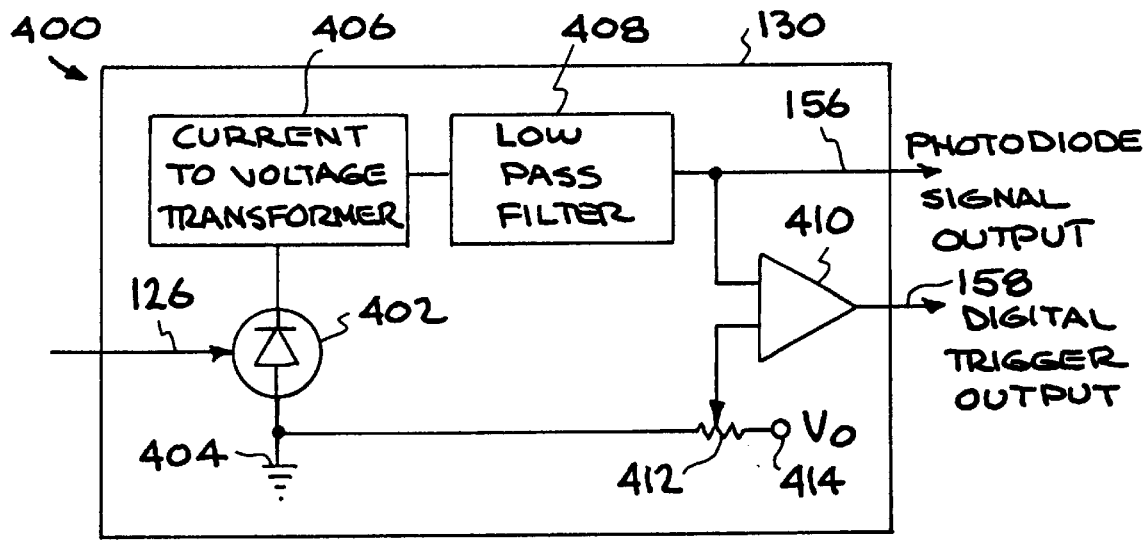
FIG. 4 is a circuit diagram of a photodiode circuit in the system of FIG. 1.

FIG. 4 is a circuit diagram 400 of the photodiode circuit 130 in the system 100 of FIG. 1. A photodiode 402 is illuminated by the back-reflected beam 126. Depending upon the position of the scanning assembly 114 over the plate 104, the photodiode 402 receives a back-reflected beam corresponding to either an air-glass, glass—glass, or gel-glass interface. The photodiode 402 is coupled between a ground 404 and a current to voltage transformer 406. The transformer 406 receives a current signal from the photodiode 402, coverts it to a voltage signal, and passes the voltage signal onto a low pass filter 408. The low pass filter 408 is a fourth-order Butterworth filter which has a cut-off frequency of about 400 Hz, and passes a filtered signal to the computer 154 over line 156 and to a comparator 410. The comparator 410 compares the filtered signal to a threshold voltage set by a tunable resistor 412. The resistor 412 is coupled between a reference voltage ($V_O$) 414 and ground 404. In an alternate embodiment, the threshold voltage may be controlled by the computer 154, using a digital to analog converter (not shown). The comparator 410 generates a digital trigger signal on line 158 when the filtered voltage exceeds the threshold voltage. This trigger signal is used by the computer 154 to indicate when the scanning assembly 114 has passed over a selected portion of the plate 104, such as one of the microchannels 102.

Figure 5:
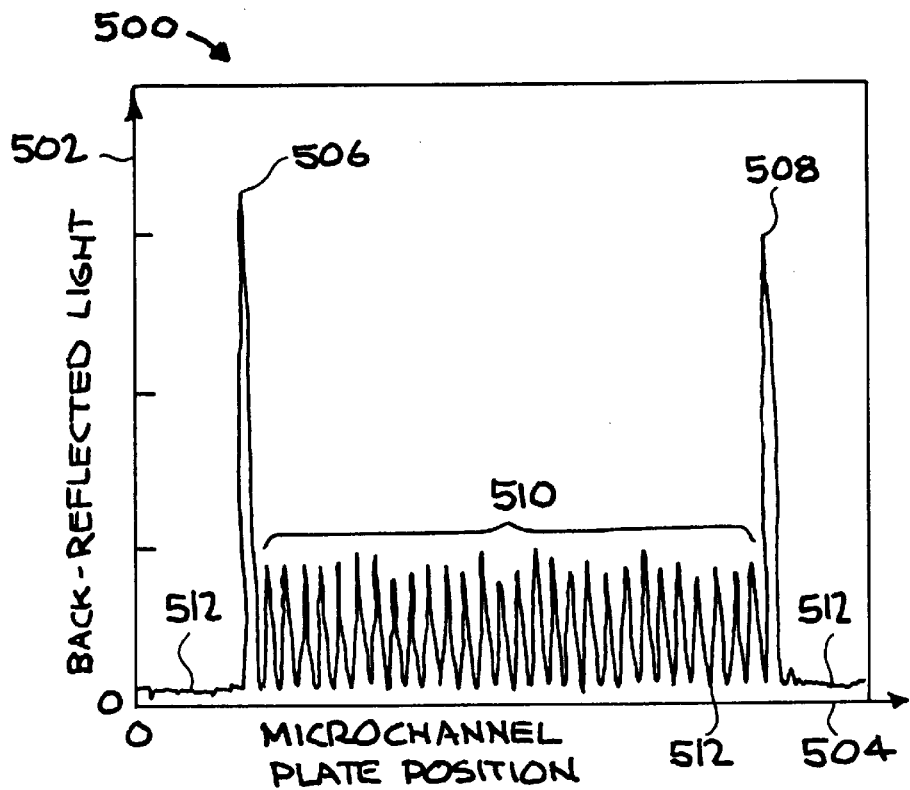
FIG. 5 is a graph of back-reflected light verses microchannel plate position.

FIG. 5 is a graph 500 of the back-reflected light 502 from the back-reflected beam 126 verses the microchannel plate position 504. The graph 500 can be generated from the computer 154 from the filtered photodiode signal on line 156, as the scanning assembly 114 moves over the microchannel plate 104. In the example shown, thirty microchannels 102 have been detected. A first channel 506 and a last channel 508 are filled with air, creating an air-glass interface which results in a large back-reflected light beam 126. Middle channels 510 are filled with gel creating a gel-glass interface which results in a small back-reflected light beam 126. A noise floor 512, before the first channel, between the middle channels, and after the last channel, represents a glass—glass interface which results in a very small back-reflected light beam 126.

Figure 6:
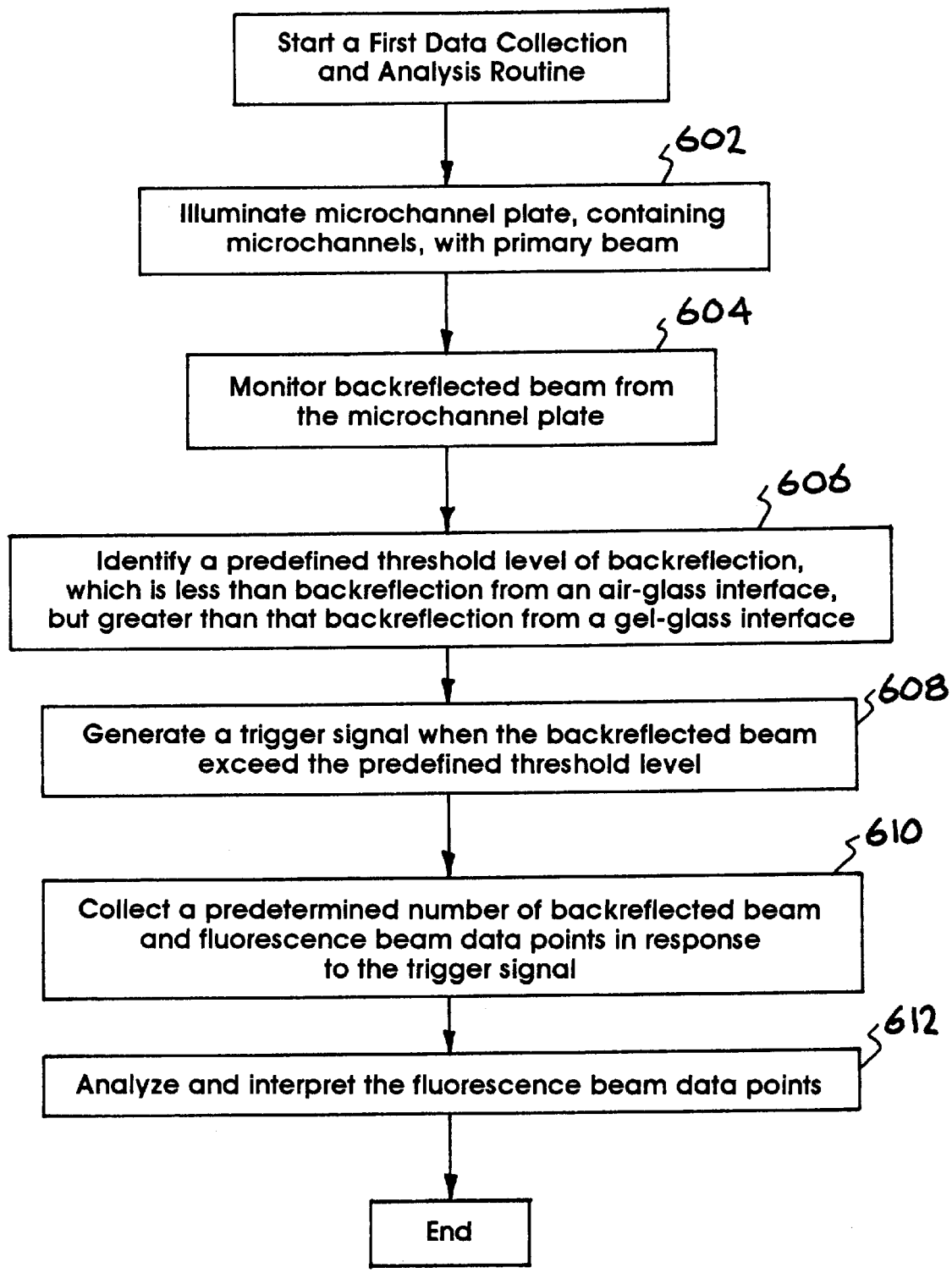
FIG. 6 is a flowchart of a first data collection and analysis method for optically locating microchannel positions.

FIG. 6 is a flowchart of a first data collection and analysis method for optically locating microchannel positions. The method begins in step 602 when the scanning assembly 114 illuminates the microchannel plate 104, containing microchannels 102, with the primary beam 120. Next, in step 604, the photodiode 402 in the photodiode circuit 130 monitors the back-reflected beam 126 from the microchannel plate 104. A predefined threshold level of back-reflection, which is less than back-reflection from an air-glass interface, but greater than that back-reflection from a gel-glass interface is identified by adjusting the variable resistor 412 either in response to a user input or automatically by the computer 154, in step 606. Next, in step 608, the comparator 410 generates a trigger signal on line 158 when the back-reflected beam exceeds the predefined threshold level. This threshold level would thus generate a trigger on the first channel 506 (ref. FIG. 5) having an air-glass interface, but not on the middle channels 510 having gel-glass interfaces. In step 610, the computer 154 collects a predetermined number of back-reflectance beam 126 and fluorescence beam 128 data points in response to the trigger signal. The predetermined number of data points are preferably just enough to cover just the channels 506, 508, and 510. This minimizes a total number of back-reflectance beam 126 and fluorescence beam 128 data points which need to be taken. If plate 104 channel spacing and scanning assembly 114 speed are already known, the trigger signal may be used as a timing reference point. A single data point could then be taken at a time when the scanning assembly 114 would be predicted to reach a center of each microchannel. The computer 154 analyzes and interprets the fluorescence beam 128 data points, in step 612. As part of this analysis, the computer 154 may condense a number of fluorescence beam data points corresponding to a single microchannel down to just one data point, using well known averaging or integration techniques. After step 612, the first method of optically locating microchannel positions is complete.

Figure 7:
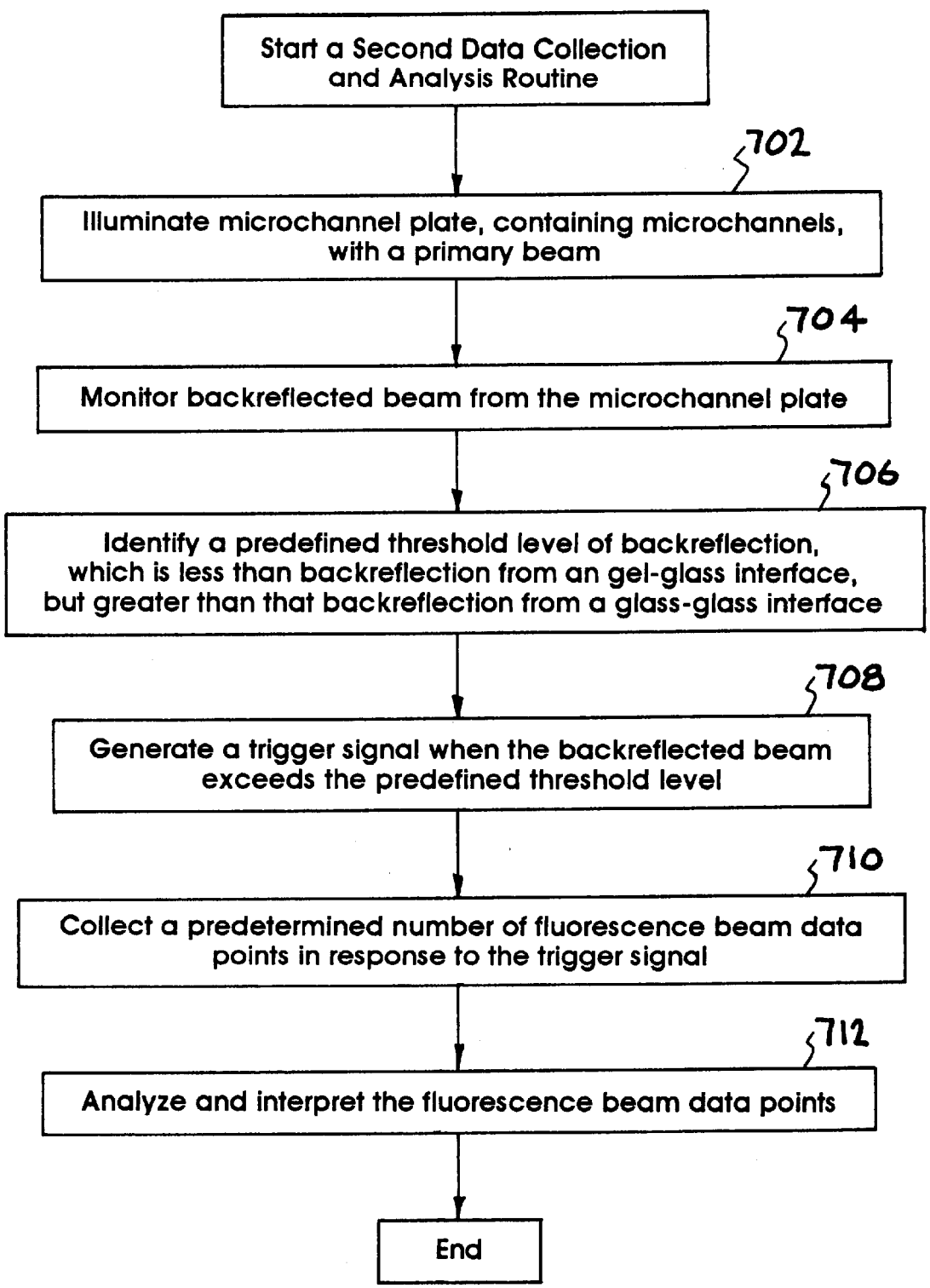
FIG. 7 is a flowchart of a second data collection and analysis method for optically locating microchannel positions.

FIG. 7 is a flowchart of a second data collection and analysis method for optically locating microchannel positions. The method begins in step 702 when the scanning assembly 114 illuminates the microchannel plate 104, containing microchannels 102, with the primary beam 120. Next, in step 704, the photodiode 402 in the photodiode circuit 130 monitors the back-reflected beam 126 from the microchannel plate 104. A predefined threshold level of back-reflection, which is less than back-reflection from a gel-glass interface, but greater than the back-reflection from a glass-glass interface is identified by adjusting the variable resistor 412 either in response to a user input or automatically by the computer 154, in step 706. Next, in step 708, the comparator 410 generates a trigger signal on line 158 when the back-reflected beam exceeds the predefined threshold level. This threshold level would thus generate a trigger on each of the channels 506, 508, and 510. In step 710, the computer 154 collects a predetermined number of fluorescence beam 128 data points in response to the trigger signal. The predetermined number of data points are preferably just enough to cover one microchannel. This minimizes a total number of fluorescence beam 128 data points which need to be taken. If microchannel 102 width and scanning assembly 114 speed are already known, the trigger signal may be used as a timing reference point. A single data point could then be taken at a time when the scanning assembly 114 would be predicted to reach a center of a microchannel. The computer 154 analyzes and interprets the fluorescence beam 128 data points, in step 712. As part of this analysis, the computer 154 may condense the number of fluorescence beam data points corresponding to a single microchannel down to just one data point, using well known averaging or integration techniques. After step 712, the first method of optically locating microchannel positions is complete.

Figure 8:
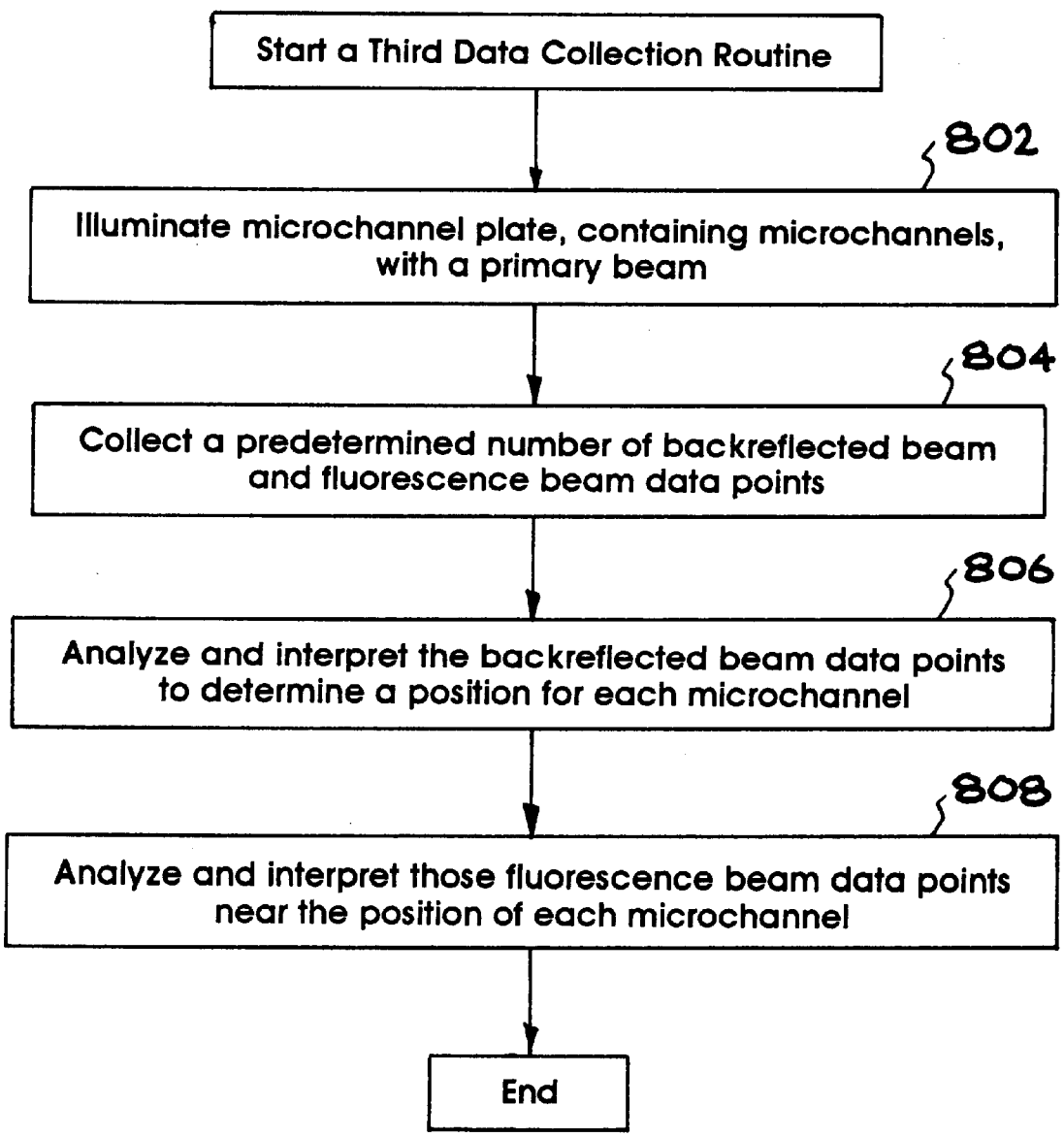
FIG. 8 is a flowchart of a third data collection and analysis method for optically locating microchannel positions.

FIG. 8 is a flowchart of a third data collection and analysis method for optically locating microchannel positions. The method begins in step 802 when the scanning assembly 114 illuminates the microchannel plate 104, containing microchannels 102, with the primary beam 120. In step 804, the computer 154 collects all of the back-reflected beam 126 data points and all the fluorescence beam 128 data points, as the scanning assembly 114 moves over the entire width of the plate 104. Next, in step 806, the computer 154 analyzes and interprets the back-reflected beam 126 data points to determine a position for each microchannel 102. The computer 154 determines these positions by effecting in software any of those triggering techniques discussed with respect to the photodiode circuit 130 hardware in FIGS. 6 and 7 above. For embodiments where the threshold voltage is controlled by the computer 154, should the triggering techniques not yield an expected number of microchannels, the computer 154 can adjust the triggering threshold levels. To reduce a time taken by the computer 154 to locate the microchannels 102, the computer 154 could be programmed to first analyze the back-reflected beam 126 data points for a reference point on the plate 104. This reference point could be created by having a predetermined pattern of air-glass microchannels at one end of the plate 104. Use of the predetermined pattern reduces a chance that random voids in the plate 104 might yield a false reference point. Once the computer 154 identifies this reference point, and accesses microchannel spacing information prestored in the memory, a position for each microchannel can be determined. In step 808, the computer 154, analyzes and interprets those fluorescence beam data points near the position of each microchannel 102. After step 808, the first method of optically locating microchannel positions is complete.

FIGS. 6, 7 and 8 represent three alternative ways of collecting and analyzing data for optically locating microchannel 102 positions and processing associated fluorescence beam 128 data. The best method to be used depends upon an environment in which the present invention is implemented. However, as a general rule, those techniques which minimize an amount of data to be collected or processed are preferred.

Adaptive techniques may also be effected in conjunction with the present invention. For example, microchannels 102 can be selectively filled with air or other media, which the computer 154 can be programmed to decode into some sort of information about the plate 104. This information may include, but is not limited to, which is a right and a left side of the plate, how many microchannels are on the plate, what is a width of a microchannel, and/or what is a spacing between the microchannels.

Those skilled in the art will recognize other ways of collecting and analyzing data for optically locating microchannel 102 positions and processing associated fluorescence beam 128 data using the microchannel position location techniques described above.

While the present invention has been described with reference to a preferred embodiment, those skilled in the art will recognize that various modifications may be made. Variations upon and modifications to the preferred embodiment are provided by the present invention, which is limited only by the following claims.

What is claimed is:

1. A system for optically locating microchannel positions, the system comprising:

a source for generating a primary beam;

a plate having a microchannel, coupled to receive the primary beam;

a beam detector, coupled to receive, from the plate, a back-reflected beam generated in response to the primary beam; and a circuit, coupled to the beam detector, for generating a trigger signal when the back-reflected beam exceeds a predetermined threshold which corresponds to a presence of the microchannel.

2. The system of claim 1, wherein the circuit generates the trigger signal when the back-reflected beam exceeds a level corresponding to a gel-glass interface and falls below a level corresponding to an air-glass interface.

3. The system of claim 1, wherein the circuit generates the trigger signal when the back-reflected beam exceeds a level corresponding to a glass—glass interface and falls below a level corresponding to a gel-glass interface.

4. The system of claim 1, further comprising:

a second beam detector, coupled to receive, from the plate, a fluorescence beam generated in response to the primary beam; and a computer, coupled to the fluorescence detector, for collecting fluorescence beam data in response to the trigger signal.

5. A method for optically locating microchannel positions, comprising the steps of:

generating a primary beam;

directing the primary beam to a plate containing a microchannel;

receiving from the plate a back-reflected beam generated in response to the primary beam; and generating a trigger signal when the back-reflected beam exceeds a predetermined threshold which corresponds to a presence of the microchannel.

6. The method of claim 5 wherein the generating a trigger signal step further includes the step of:

setting the predetermined threshold level below a back-reflected beam generated from an air-glass interface.

7. The method of claim 6 wherein the generating a trigger signal step further includes the step of:
setting the predetermined threshold level above a back-reflected beam generated from a gel-glass interface.

8. The method of claim 5 wherein the generating a trigger signal step further includes the step of:
setting the predetermined threshold level below a back-reflected beam generated from a gel-glass interface.

9. The method of claim 8 wherein the generating a trigger signal step further includes the step of:
setting the predetermined threshold level above a back-reflected beam generated from a glass—glass interface.

10. The method of claim 5 further including the steps of:
receiving from the plate a fluorescence beam generated in response to the primary beam; and
collecting a predetermined amount of fluorescence beam data in response to the trigger signal.

11. The method of claim 5 further including the step of:
collecting a predetermined amount of back-reflected beam data in response to the trigger signal.

12. A method for optically locating microchannel positions, comprising the steps of:
generating a primary beam;
directing the primary beam to a plate containing a microchannel;
receiving from the plate a back-reflected beam generated in response to the primary beam;
collecting a predetermined amount of back-reflected beam data; and
determining a position of the microchannel by analyzing the back-reflected beam data.

13. The method of claim 12 wherein the determining step further includes the step of:
defining a reference pattern of back-reflectance on the plate;
analyzing the back-reflected beam data for the reference pattern;
accessing predetermined microchannel spacing information; and
determining the position of the microchannel.

14. The method of claim 12 further including the step of:
receiving from the plate a fluorescence beam generated in response to the primary beam;
collecting a predetermined amount of fluorescence beam data; and
analyzing those fluorescence beam data points near the position of the microchannel.

15. A system for optically locating microchannel positions, comprising:
means for generating a primary beam;
means for directing the primary beam to a plate containing a microchannel;
means for receiving from the plate a back-reflected beam generated in response to the primary beam; and
means for generating a trigger signal when the back-reflected beam exceeds a predetermined threshold which corresponds to a presence of the microchannel.

16. The system of claim 15 further including:
means for receiving from the plate a fluorescence beam generated in response to the primary beam; and
means for collecting a predetermined amount of fluorescence beam data in response to the trigger signal.

17. The system of claim 15 further including:
means for collecting a predetermined amount of back-reflected beam data in response to the trigger signal.

18. A system for optically locating microchannel positions, comprising:
means for generating a primary beam;
means for directing the primary beam to a plate containing a microchannel;
means for receiving from the plate a back-reflected beam generated in response to the primary beam;
means for collecting a predetermined amount of back-reflected beam data; and
means for determining a position of the microchannel by analyzing the back-reflected beam data.

19. The system of claim 18 further including:
means for receiving from the plate a fluorescence beam generated in response to the primary beam;
means for collecting a predetermined amount of fluorescence beam data; and
means for analyzing those fluorescence beam data points near the position of the microchannel.

20. A computer-usable medium embodying computer program code for causing a computer to optically locate microchannel positions, by performing the steps of:
generating a primary beam;
directing the primary beam to a plate containing a microchannel;
receiving from the plate a back-reflected beam generated in response to the primary beam; and
generating a trigger signal when the back-reflected beam exceeds a predetermined threshold which corresponds to a presence of the microchannel.

21. The computer-usable medium of claim 20 further performing the steps of:
receiving from the plate a fluorescence beam generated in response to the primary beam; and
collecting a predetermined amount of fluorescence beam data in response to the trigger signal.

22. The computer-usable medium of claim 20 further performing the step of:
collecting a predetermined amount of back-reflected beam data in response to the trigger signal.

23. A computer-usable medium embodying computer program code for causing a computer to optically locate microchannel positions, by performing the steps of:
generating a primary beam;
directing the primary beam to a plate containing a microchannel;
receiving from the plate a back-reflected beam generated in response to the primary beam;
collecting a predetermined amount of back-reflected beam data; and
determining a position of the microchannel by analyzing the back-reflected beam data.

24. The computer-usable medium of claim 23 further performing the step of:
receiving from the plate a fluorescence beam generated in response to the primary beam;
collecting a predetermined amount of fluorescence beam data; and
analyzing those fluorescence beam data points near the position of the microchannel.

25. A system for optically locating microchannel positions in an electrophoresis process, the system comprising:

a source for generating a primary beam;

a plate having a microchannel coupled to receive the primary beam;

a beam detector, coupled to receive, from the plate a back-reflected beam generated in response to the primary beam; and a circuit coupled to the beam detector which generates a trigger signal when the back-reflected beam exceeds a predetermined threshold which corresponds to a presence of the microchannel.

26. A method for optically locating microchannel positions in an electrophoresis process comprising the steps of:

generating a primary beam;

directing the primary beam to a plate containing a microchannel;

receiving from the plate a back-reflected beam generated in response to the primary beam; and generating a signal when the back-reflected beam exceeds a predetermined threshold which corresponds to a presence of the microchannel.

27. A system for optically locating microchannel positions, the system comprising:

a source for generating a primary beam;

a plate having a microchannel coupled to receive the primary beam and wherein said plate is stationary during scanning by said primary beam;

a beam detector coupled to receive from the plate a back-reflected beam generated in response to the primary beam during scanning; and a circuit coupled to the beam detector which generates a trigger signal when the back-reflected beam indicates a presence of the microchannel.

28. A system for optically locating microchannel positions, the system comprising:

a source for generating a primary beam;

a plate having a microchannel coupled to receive the primary beam;

said primary beam moving perpendicularly to the longitudinal axis of the plate during scanning while the plate remains stationary;

a beam detector coupled to receive from the plate a back-reflected beam generated in response to the primary beam during scanning; and a circuit coupled to the beam detector which generates a trigger signal when the back-reflected beam indicates a presence of the microchannel.

29. A system for optically locating microchannel positions, the system comprising:

a source for generating a primary beam;

a plurality of plates forming a plurality of microchannels adapted to contain fluidic material and coupled to receive the primary beam;

a beam detector coupled to receive from the plates a back-reflected beam generated in response to the primary beam during scanning; and a circuit coupled to the beam detector which generates a trigger signal when the back-reflected beam indicates a presence of the microchannels.

30. A system for optically locating microchannel positions, the system comprising:

a source for generating a primary beam;

a plurality of plates having a microchannel coupled to receive the primary beam;

a first and second beam detectors coupled to receive from the plurality of plates a back-reflected, fluorescence beam generated in response to the primary beam;

a first circuit coupled to the first beam detector which generates a trigger signal when the back-reflected beam exceeds a predetermined threshold which corresponds to a presence of the microchannel; and a computer coupled to the second detector which collects fluorescence beam data in response to the trigger signal.

* * * * *